US012569993B2

(12) United States Patent
Watanabe et al.

(10) Patent No.: US 12,569,993 B2
(45) Date of Patent: Mar. 10, 2026

(54) DETERMINATION DEVICE AND POSTURE CONTROL DEVICE

(71) Applicants: TAKENAKA CIVIL ENGINEERING & CONSTRUCTION CO., LTD., Tokyo (JP); NATIONAL UNIVERSITY CORPORATION TOKYO UNIVERSITY OF MARINE SCIENCE AND TECHNOLOGY, Tokyo (JP)

(72) Inventors: Yutaka Watanabe, Tokyo (JP); Masahiro Hamana, Tokyo (JP)

(73) Assignees: TAKENAKA CIVIL ENGINEERING & CONSTRUCTION CO., LTD., Tokyo (JP); NATIONAL UNIVERSITY CORPORATION TOKYO UNIVERSITY OF MARINE SCIENCE AND TECHNOLOGY, Tokyo (JP)

( * ) Notice: Subject to any disclaimer, the term of this patent is extended or adjusted under 35 U.S.C. 154(b) by 484 days.

(21) Appl. No.: 17/760,293

(22) PCT Filed: Feb. 6, 2020

(86) PCT No.: PCT/JP2020/004615
§ 371 (c)(1),
(2) Date: Aug. 5, 2022

(87) PCT Pub. No.: WO2021/157026
PCT Pub. Date: Aug. 12, 2021

(65) Prior Publication Data
US 2023/0083094 A1 Mar. 16, 2023

(51) Int. Cl.
B25J 9/16 (2006.01)
A61B 5/00 (2006.01)
A61B 5/11 (2006.01)

(52) U.S. Cl.
CPC ............. B25J 9/1664 (2013.01); A61B 5/112 (2013.01); A61B 5/4561 (2013.01); *A61B 2562/0219* (2013.01)

(58) Field of Classification Search
CPC ...... B25J 9/1664; B25J 9/1602; B25J 9/1679; A61B 5/112; A61B 5/4561;
(Continued)

(56) References Cited

U.S. PATENT DOCUMENTS 6,198,951 B1 * 3/2001 Kosuda ................ A61B 5/6826
600/323
2005/0066397 A1 * 3/2005 Hidai ................... B62D 57/032
901/1
(Continued)

FOREIGN PATENT DOCUMENTS

JP 2004081745 A 3/2004
JP 200528157 A 2/2005
(Continued)

OTHER PUBLICATIONS

"Sina Ameli; David Stirling; Fazel Naghdy; Golshah Naghdy; Morteza Aghmesheh, Assessing the impact of fatigue on gait using inertial sensors, Aug. 22, 2013, IEEE") (Year: 2013).*
(Continued)

*Primary Examiner* — Ramon A. Mercado
(74) *Attorney, Agent, or Firm* — Alleman Hall LLP

(57) ABSTRACT

A determination device includes: a sway detector that detects sway of a person when the person moves; and a controller. The determination device performs spectrum analysis by resolving sway data outputted from the sway detector into frequency components. In a spectrum obtained from the spectrum analysis, a first peak, a second peak, and a third peak sequentially appear in order of increasing frequency. The controller determines a state of a body of the
(Continued)

person based on the first peak, the second peak, and the third peak.

6 Claims, 12 Drawing Sheets

(58) Field of Classification Search
    CPC ........ A61B 2562/0219; A61B 2503/20; A61B
                5/1121; A61B 5/6803; A61B 5/7257;
                A61B 5/7275; A61B 5/1036; B62D 57/02
    See application file for complete search history.

(56)                    References Cited

U.S. PATENT DOCUMENTS

| | | | | |
|---|---|---|---|---|
| 2005/0075553 | A1* | 4/2005 | Sakai | A61B 5/4035 |
| | | | | 600/372 |
| 2010/0137748 | A1 | 6/2010 | Sone et al. | |
| 2017/0296101 | A1* | 10/2017 | Alberts | A61B 5/1116 |
| 2022/0233390 | A1* | 7/2022 | Kuhn | B25J 9/1605 |

FOREIGN PATENT DOCUMENTS

| | | | | |
|---|---|---|---|---|
| JP | 2005160640 | A | | 6/2005 |
| JP | 2005342254 | A | | 12/2005 |
| JP | 201641155 | A | | 3/2016 |
| JP | 2016041155 | A | * | 3/2016 |
| KR | 102422132 | B1 | * | 11/2019 |
| WO | 2018079377 | A1 | | 5/2018 |
| WO | WO-2022272170 | A1 | * | 12/2022 |

OTHER PUBLICATIONS

"NURSEFUL Disorder-Specific Series, Orthopedics, Chapter 1, Anatomy and Functions of Bones, Nerves, and Skeletal Muscles," Recruit (C) Recruit Medical Career Co., Ltd., Available Online at https://nurseful.jp/nursefulshikkanbetsu/orthopedics/section_0_00/, Available as early as Mar. 8, 2020, 28 pages.

* cited by examiner

100

10

$$(A_m \geq A_l > A_t \, , \, A_l > (A_m + A_t)/2)$$

$$(A_m \geq A_l > A_t, A_l \leq (A_m + A_t)/2)$$

200

DETERMINATION DEVICE AND POSTURE CONTROL DEVICE

TECHNICAL FIELD

The present disclosure relates to a determination device and a posture control device.

BACKGROUND ART

Precise real-time detection of the state, posture, etc. of the body of a person makes it possible to obtain useful information in various fields. For example, Patent Literature 1 discloses a technique for estimating the walking state, posture, etc. of a person based on signals from an accelerometer mounted on the body of the person.

CITATION LIST

Patent Literature

PTL 1: Japanese Laid-Open Patent Application Publication No. 2016-4115≡

SUMMARY OF INVENTION

Technical Problem

As one example, an objective of the present disclosure is to provide a determination device that is capable of determining the state of the body of a person more precisely and in a simpler manner than conventional art.

Solution to Problem

A determination device of one aspect of the present disclosure includes: a sway detector that detects sway of a person when the person moves; and a controller. The determination device performs spectrum analysis by resolving sway data outputted from the sway detector into frequency components. In a spectrum obtained from the spectrum analysis, a first peak, a second peak, and a third peak sequentially appear in order of increasing frequency. The controller determines a state of a body of the person based on the first peak, the second peak, and the third peak.

Advantageous Effects of Invention

The determination device of the one aspect of the present disclosure provides an advantageous effect of being able to determine the state of the body of a person more precisely and in a simpler manner than conventional art.

DESCRIPTION OF EMBODIMENTS

[Background that has LED to a Determination Device of One Aspect of the Present Disclosure]

The present discloser has been conducting research and development for theoretically deriving the position of the three-dimensional center of gravity (which may be hereinafter simply referred to as "the center of gravity") of a traveling unit in the logistics industry (e.g., a cargo container vehicle) by using a sway detector mounted on the traveling unit. The results achieved by the research and development are partly disclosed in a prior patent (e.g., Japanese Patent No. 4517107).

In the course of the research and development, the present discloser has noticed that the above results are useful in determining the state of the body of a person.

Specifically, every physical object has its three-dimensional center of weight (the center of gravity). If the center of gravity of the physical object is stable against external disturbance, the physical object can maintain its posture. This also applies to a person. That is, the state of the body of a person is considered to be closely related to a physical phenomenon, specifically, closely related to whether the center of gravity of the body of the person is stable against external disturbance.

For example, the center of gravity of a human body is supported by the skeleton and muscles. Since a human body is bilaterally symmetrical, the present discloser has assumed a human body as a bilaterally symmetrical spring structure, and has assumed that the overall human body can be modeled. If these assumptions are correct, the position of the center of gravity of a person can be known based on the theory disclosed in the aforementioned prior patent.

In consideration of the above, first, the present discloser modeled a human body in the state of walking, measured sway data of a person while the person was walking, and performed spectrum analysis of the sway data obtained while the person was walking. Then, the present discloser derived the position of the center of gravity of the person based on the theory disclosed by the aforementioned prior patent.

<Modeling of a Human Body (a Spring Structure) in the State of Walking>

Figure 1:
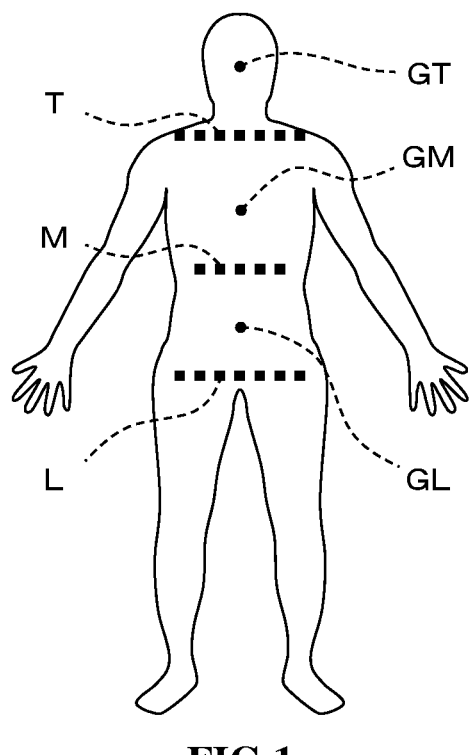
FIG. 1 shows one example of modeling of a human body in the state of walking.

FIG. 1 shows one example of modeling of a human body in the state of walking.

According to Literature 1 indicated below, in a human body, the entire body part above the femurs is supported by the lower extremity.

Literature 1: "NURSEFUL Disorder-Specific Series, Orthopedics, Chapter 1, Anatomy and Functions of Bones, Nerves, and Skeletal Muscles" [Translated from Japanese.], RECRUIT (C) Recruit Medical Career Co., Ltd.

Since the lower extremity is a structure that allows rotational motion to the left and right, the lower extremity is a spring structure. The body from the chest upward is supported by the spinal column positioned above the lower extremity. The spinal column is made up of 24 vertebrae. Since the spinal column is supported by muscles such as the abdominal muscles, the spinal column is a structure that allows rotational motion to the left and right. From the clavicles upward, the muscles support the head, and the cervical spine (the upper part of the spinal column) is a structure that allows rotational motion of the head to the left and right.

Therefore, as shown in FIG. 1, the present discloser has come to an understanding that when a human walks, the human's body posture is held at: a center of gravity GL of the entire body supported by a lower extremity spring base L; a center of gravity GM of the upper part of the chest supported by a spinal column spring base M; and a center of gravity GT of the head supported by a clavicle spring base T. Then, the present discloser has come to a conclusion that it is appropriate to model the human body in the state of walking as shown in FIG. 1.

<Spectrum Analysis of Sway Data>

A test subject [1], a test subject [2], and a test subject [3] (which may be simply referred to as "test subjects" or "each test subject" in the description below) each wearing an engineer helmet with a sway detector fixed thereto walked on a flat road. Then, sway data outputted from each sway detector was obtained. Specifically, angular velocity data of sway during each test subject walking was measured in a lateral direction orthogonal to the walking direction of each test subject (i.e., measured in the width direction of the body of each test subject), and also, acceleration data of sway during each test subject walking was measured in the vertical direction (which may alternatively be referred to as "the perpendicular direction" in the description below) in which the gravitational force was exerted.

Test subject [1]: a female in her early twenties (short and slender)

Test subject [2]: a male in his early twenties (tall and slender)

Test subject [3]: a male in his late fifties (medium height and medium build)

Figure 2A:
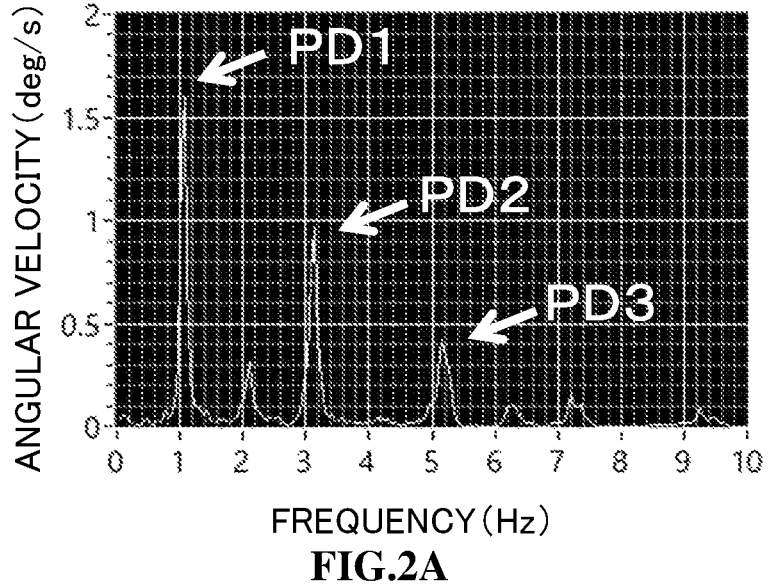
FIG. 2A shows one example of results of analyzing sway data outputted from a sway detector during a test subject [1] walking.
Figure 2B:
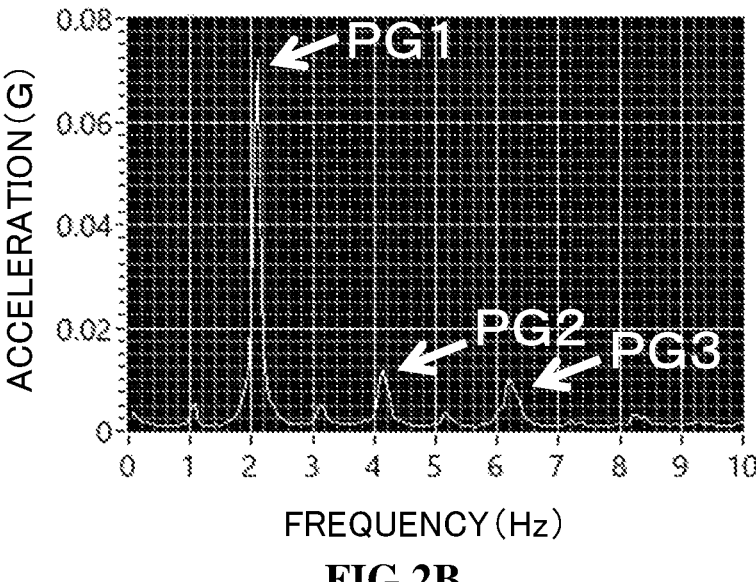
FIG. 2B shows one example of results of analyzing sway data outputted from the sway detector during the test subject [1] walking.

FIG. 2A and FIG. 2B show one example of results of analyzing the sway data outputted from the sway detector during the test subject [1] walking.

Figure 3A:
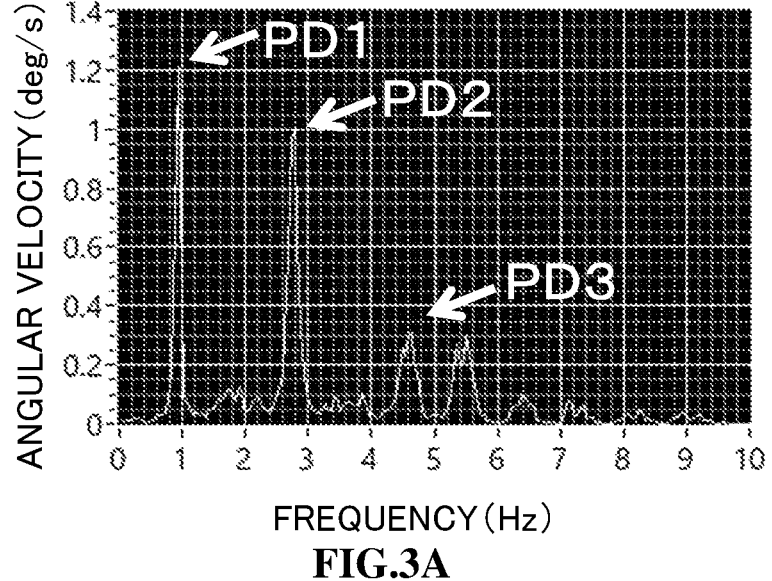
FIG. 3A shows one example of results of analyzing sway data outputted from the sway detector during a test subject [2] walking.
Figure 3B:
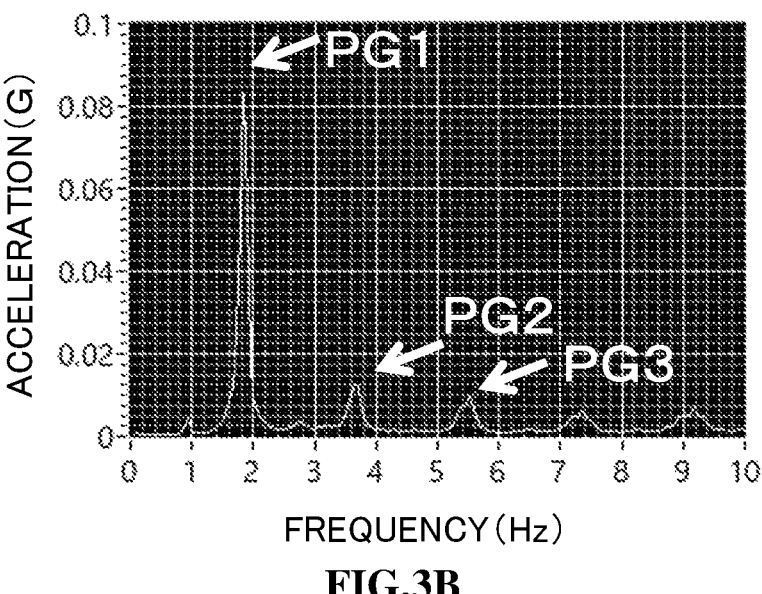
FIG. 3B shows one example of results of analyzing sway data outputted from the sway detector during the test subject [2] walking.

FIG. 3A and FIG. 3B show one example of results of analyzing the sway data outputted from the sway detector during the test subject [2] walking.

Figure 4A:
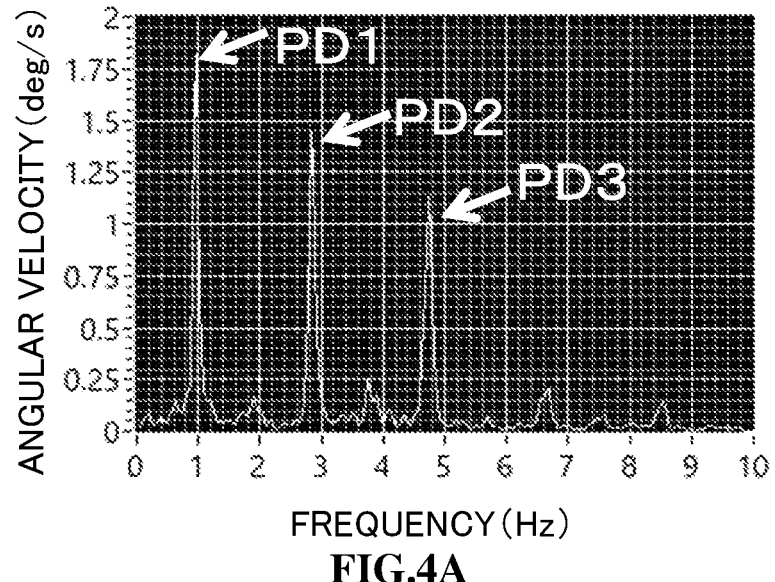
FIG. 4A shows one example of results of analyzing sway data outputted from the sway detector during a test subject [3] walking.
Figure 4B:
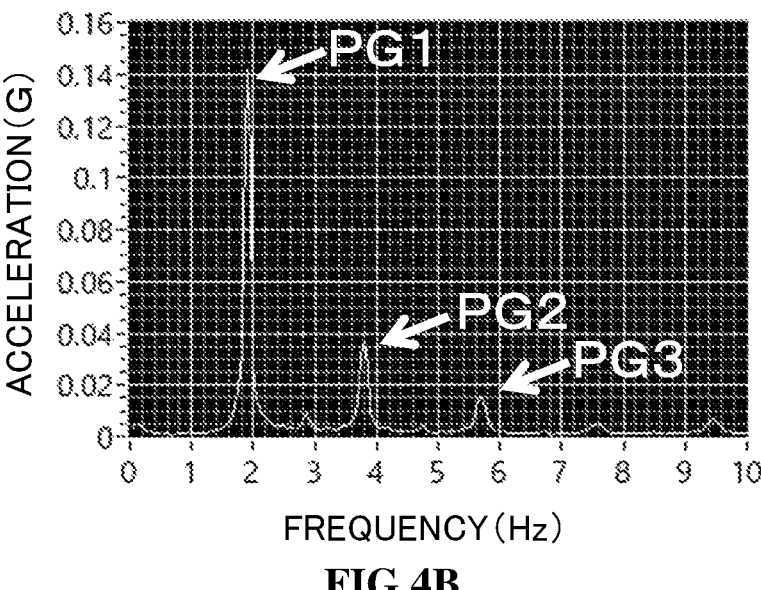
FIG. 4B shows one example of results of analyzing sway data outputted from the sway detector during the test subject [3] walking.

FIG. 4A and FIG. 4B show one example of results of analyzing the sway data outputted from the sway detector during the test subject [3] walking.

In FIG. 2A, FIG. 3A, and FIG. 4A, the horizontal axis represents frequency (Hz) and the vertical axis represents angular velocity (deg/s). The aforementioned angular velocity data is resolved into frequency components, and thereby the results of spectrum analysis of the angular velocity are shown in FIG. 2A, FIG. 3A, and FIG. 4A. Specifically, in FIG. 2A, FIG. 3A, and FIG. 4A, chronological angular velocity data measured by each sway detector is subjected to Fourier transformation to specify peak frequencies of the angular velocity, the peak frequencies being derived from sways of the centers of gravity of each test subject in the lateral direction during the test subject walking.

In FIG. 2B, FIG. 3B, and FIG. 4B, the horizontal axis represents frequency (Hz) and the vertical axis represents acceleration (G). The aforementioned acceleration data is resolved into frequency components, and thereby the results of spectrum analysis of the acceleration are shown in FIG. 2B, FIG. 3B, and FIG. 4B. Specifically, in FIG. 2B, FIG. 3B, and FIG. 4B, chronological acceleration data measured by each sway detector is subjected to Fourier transformation to specify peak frequencies of the acceleration, the peak frequencies being derived from sways of the centers of gravity of each test subject in the perpendicular direction during the test subject walking.

It should be noted that since the sway detector cannot completely eliminate mutual interference between sensitivity axes, the angular velocity spectrum shown in each of FIG. 2A, FIG. 3A, and FIG. 4A is interfered with by accelerations derived from the sways of the centers of gravity of each test subject in the perpendicular direction, and vice versa. Therefore, in FIGS. 2A and 2B, FIGS. 3A and 3B, and FIGS. 4A and 4B, slight waveforms caused by the aforementioned mutual interference are shown.

A shown in each of FIG. 2A, FIG. 3A, and FIG. 4A, in the spectrum obtained from the spectrum analysis, a first angular velocity peak PD1, a second angular velocity peak PD2, and a third angular velocity peak PD3 sequentially appear in order of increasing frequency. Amplitudes (angular velocity values represented by the vertical axis in each of FIG. 2A, FIG. 3A, and FIG. 4A) corresponding to the first angular velocity peak PD1, the second angular velocity peak PD2, and the third angular velocity peak PD3, respectively, decrease in this order.

As shown in each of FIG. 2B, FIG. 3B, and FIG. 4B, in the spectrum obtained from the spectrum analysis, a first acceleration peak PG1, a second acceleration peak PG2, and a third acceleration peak PG3 sequentially appear in order of increasing frequency. Amplitudes (acceleration values represented by the vertical axis in each of FIG. 2B, FIG. 3B, and FIG. 4B) corresponding to the first acceleration peak PG1, the second acceleration peak PG2, and the third acceleration peak PG3, respectively, decrease in this order.

When a person walks, the person hardly feels sway at their chest and head, but on the other hand, it has empirically been known that the degree of sway (amplitude) is great at the lower extremity.

Theoretically speaking, when a physical object vibrates due to external force, the greater the mass of the physical object, the slower the vibrating motion of the center of gravity of the physical object. That is, the greater the mass of the physical object, the less the frequency of sway of the center of gravity of the physical object.

In view of the above, considering the modeling of a human body as shown in FIG. 1, since the weight of the entire body of each test subject, which is supported by the lower extremity spring base L, is the greatest weight supported, the first angular velocity peak PD1 and the first acceleration peak PG1 are each assumed to be a peak derived from sway of the center of gravity GL existing above the lower extremity of the person, the sway occurring when the person walks.

Since the weight of the head, which is supported by the clavicle spring base T, is the smallest weight supported, the third angular velocity peak PD3 and the third acceleration peak PG3 are each assumed to be a peak derived from sway of the center of gravity GT existing at the head of the person, the sway occurring when the person walks.

Since the weight of the chest, which is supported by the spinal column spring base M, is a value between the weight of the entire body and the weight of the head, the second angular velocity peak PD2 and the second acceleration peak PG2 are each assumed to be a peak derived from sway of the center of gravity GM existing at the upper chest of the person, the sway occurring when the person walks.

Table 1 (see below) shows, based on the above assumptions, peak frequencies derived from sways of the centers of gravity when each of the test subject [1], the test subject [2], and the test subject [3] walked.

orthogonal to the walking direction of the person. Therefore, an arithmetic formula representing such a center of gravity displacement, the arithmetic formula being disclosed in the aforementioned prior patent, is not taken into consideration in the description herein.

[Math. 1]

$$(1+\tan^2\alpha)l^2 + \left(\frac{g}{4\pi^2 v'^2 \cos\alpha} - \frac{2\pi^2 v'^2 b^2}{g}\tan^2\alpha\right)l + \frac{\pi^4 v'^4 b^4}{g^2}\tan^2\alpha - \frac{b^2 v'^2}{4v^2 \cos\alpha} = 0 \tag{1}$$

In the equation (1), l is the height of a center of gravity; a is a sway center angle; b is the width of a spring base; v' is the frequency of acceleration; v is the frequency of an angular velocity; g is gravitational acceleration; and $\pi$ is the circular constant. Since the derivation method of the equation (1) and so forth can be readily understood by referring to the aforementioned prior patent, the description thereof is omitted herein.

Generally speaking, in the case of a person with no lower extremity disability, often there is no center of gravity displacement in the lateral direction. For this reason, sway center angle $\alpha$ can be assumed to be zero ($\alpha$=0). Therefore, the equation (1) can be simplified as an equation (2) shown below.

[Math. 2]

$$l^2 + \frac{g}{4\pi^2 v^2}l - \frac{b^2 v'^2}{4v^2} = 0 \tag{2}$$

By assigning the frequencies indicated in the above Table 1 to the equation (2), a height L1 of the center of gravity GL from the lower extremity spring base L (see FIG. 5), a height L2 of the center of gravity GM from the spinal column

TABLE 1

| | | Test subject [1] | | Test subject [2] | | Test subject [3] | |
|---|---|---|---|---|---|---|---|
| | Center of gravity | Frequency (Hz) | Multiple | Frequency (Hz) | Multiple | Frequency (Hz) | Multiple |
| Angular speed | Above lower extremity (GL) | 1.013 | | 0.882 | | 0.912 | |
| | Upper chest (GM) | 3.069 | 3.03 | 2.711 | 3.07 | 2.799 | 3.07 |
| | Head (GT) | 5.123 | 5.06 | 4.570 | 5.18 | 4.697 | 5.15 |
| Acceleration | Above lower extremity (GL) | 2.046 | | 1.800 | | 1.862 | |
| | Upper chest (GM) | 4.101 | 2.00 | 3.635 | 2.02 | 3.750 | 2.01 |
| | Head (GT) | 6.155 | 3.01 | 5.472 | 3.04 | 5.634 | 3.03 |

<Derivation of the Positions of Centers of Gravity of a Person>

Next, based on the disclosure in the aforementioned prior patent (Japanese Patent No. 4517107), the positions of the above three centers of gravity, i.e., the center of gravity GL, the center of gravity GM, and the center of gravity GT, during a person walking were derived.

According to the aforementioned prior patent, the height of the center of gravity of a bilaterally symmetrical spring structure is represented by an equation (1) shown below. It should be noted that while a person with no lower extremity disability is walking, it is often the case that there is no center of gravity displacement in the lateral direction spring base M (see FIG. 5), and a height L3 of the center of gravity GT from the clavicle spring base T (see FIG. 5) can be derived for each test subject.

However, in order to determine the height of each center of gravity with the equation (2), it is necessary to know the width b of the spring base.

According to the aforementioned Literature 1, in a human body, the hip joint width is equal to the shoulder width (the shoulder width is the distance between a position where one clavicle and one scapula intersect and a position where the other clavicle and the other scapula intersect). One of these positions corresponds to the center of an assembly of the left-side muscles, and the other position corresponds to the center of an assembly of the right-side muscles. Accordingly, among the lower extremity spring base L, the spinal column spring base M, and the clavicle spring base T, a width B1 (see FIG. 5) of the lower extremity spring base L and a width B3 (see FIG. 5) of the clavicle spring base T are substantially the same.

Meanwhile, the region of the spinal column spring base M is an assembly of the abdominal muscles that contract toward the spinal column. Accordingly, a width B2 (see FIG. 5) of the spinal column spring base M is slightly less than the width B1 and the width B3. From analogical inference based on the disclosure of Literature 1, the width B2 of the spinal column spring base M is considered to be about 95% of each of the width B1 and the width B3.

In light of the above, for each test subject, the width b of the spring base in the equation (2) can be known, for example, by actually measuring the width B3 of the clavicle spring base T.

In the above-described manner, the height L1 of the center of gravity GL from the lower extremity spring base L, the height L2 of the center of gravity GM from the spinal column spring base M, and the height L3 of the center of gravity GT from the clavicle spring base T were obtained for each test subject, and the numerical values of these obtained heights were as indicated below.

Test subject [1]: L1=0.141 m, L2=0.133 m, L3=0.134 m
Test subject [2]: L1=0.150 m, L2=0.150 m, L3=0.150 m
Test subject [3]: L1=0.146 m, L2=0.144 m, L3=0.144 m When taking the physical attributes of a normal adult person into consideration, the above heights of the centers of gravity are data backing up the following. In a case where a person is walking, the three peaks sequentially appearing in order of increasing frequency in the spectrum obtained from the above spectrum analysis are as follows: a peak derived from sway of the center of gravity GL, which exists below the region of the spinal column spring base M and exists above the lower extremity of the person; a peak derived from sway of the center of gravity GM, which exists below the region of the clavicle spring base T and exists at the upper chest of the person; and a peak derived from sway of the center of gravity GT, which exists at the head of the person.

Accordingly, the three peaks appearing in the spectrum obtained from the above spectrum analysis are considered to be useful information for determining the state of the body of a person.

Specifically, a determination device of a first aspect of the present disclosure includes: a sway detector that detects sway of a person when the person moves; and a controller. The determination device performs spectrum analysis by resolving sway data outputted from the sway detector into frequency components. In a spectrum obtained from the spectrum analysis, a first peak, a second peak, and a third peak sequentially appear in order of increasing frequency. The controller determines a state of a body of the person based on the first peak, the second peak, and the third peak.

According to the above configuration, the determination device of the first aspect is capable of determining the state of the body of the person more precisely and in a simpler manner than conventional art.

For example, at civil engineering construction sites, due to workers' accumulated fatigue caused by a high-temperature and high-humidity condition in summer, various problems occur, such as deterioration in workers' physical condition, lowered work efficiency, and the occurrence of errors during the work. In recent years, these problems have been drawing attention. Generally known methods for determining the level of fatigue of a person include blood sugar level detection, heart rate measurement, etc. However, these data are significantly affected by, for example, lifestyle habits of individuals. Therefore, with these data, it is difficult to clearly indicate the level of fatigue of a person based on, for example, standardized numerical value ranges or standardized indexes. Moreover, it is impossible to measure the accumulation of fatigue of a person in real time with existing medical determination in which the determination is made by performing a close examination of the person at a hospital. Thus, such way of medical determination is not suitable for determining the level of fatigue of a person who works at, for example, a work site in the civil engineering construction industry or logistics industry.

A person tends to feel unsteady on their feet due to factors such as fatigue and lack of sleep. For example, if a person starts feeling fatigue while performing some task, the person tends to totter at the time of walking. As the fatigue accumulates, the tottering becomes more significant, and in some cases, it becomes difficult for the person to walk.

The present discloser conducted diligent studies, and as a result of the studies, the present discloser has found that between a normal time when a person is not feeling accumulated fatigue and an abnormal time when the person is feeling accumulated fatigue, there is a clear difference in terms of tottering of the person. The present discloser has further found that the level of fatigue of a person can be precisely determined in real time based on a magnitude relationship among amplitudes corresponding to the peaks derived from sways in the horizontal direction, the peaks appearing in the aforementioned spectrum. Consequently, the present discloser has arrived at a below-described aspect of the present disclosure.

Specifically, a determination device of a second aspect of the present disclosure is configured such that, in the determination device of the first aspect, the sway detector includes an angular velocity sensor that detects an angular velocity of sway of the person in a horizontal direction when the person moves, the horizontal direction being orthogonal to a direction in which gravitational force is exerted; the first peak, the second peak, and the third peak include a first angular velocity peak, a second angular velocity peak, and a third angular velocity peak, respectively; and the controller determines a level of fatigue of the person based on a magnitude relationship among a first amplitude corresponding to the first angular velocity peak, a second amplitude corresponding to the second angular velocity peak, and a third amplitude corresponding to the third angular velocity peak.

A determination device of a third aspect of the present disclosure is configured such that, in the determination device of the third aspect, the first angular velocity peak is a peak that is derived from sway, in the horizontal direction, of a center of gravity existing above a lower extremity of the person; the second angular velocity peak is a peak that is derived from sway, in the horizontal direction, of a center of gravity existing at an upper chest of the person; and the third angular velocity peak is a peak that is derived from sway, in the horizontal direction, of a center of gravity existing at a head of the person.

According to the above configurations, the determination device of each aspect is capable of properly determining the level of fatigue of a person based on universal criteria that are related to sways of the centers of gravity existing in the person and that are hardly affected by, for example, the lifestyle habits of individuals. According to the determination device of each of the above aspects, for example, at a work site in the civil engineering construction industry or logistics industry, by merely attaching the sway detector to a worker, the level of fatigue of the worker can be readily determined in real time.

As previously described, the state of the body of a person is considered to be closely related to a physical phenomenon, specifically, closely related to whether the center of gravity of the body of the person is stable against external disturbance. In light of this, the present discloser further studied the three peak frequencies appearing in the spectrum obtained from the above spectrum analysis.

<Stable Resonation Phenomenon of Sways of Centers of Gravity>

First, in the present specification, vibration phenomena of a physical object are defined as explained below. Vibration phenomena are roughly categorized into the following two types of phenomena.

One vibration phenomenon is that different forced vibrations having the same natural period overlap each other, and in this phenomenon, the amplitudes are amplified unstably. In this case, it is possible that the vibration system becomes unstable and eventually broken. This phenomenon is called unstable resonation.

The other vibration phenomenon is that when one forced vibration is applied to another physical object that has been stationary, this other physical object starts vibrating with its own natural period. However, since this other physical object has no forced vibration, the degree of vibration is stable, and no divergent vibration is caused, i.e., the vibration is calm. This phenomenon is called stable resonation.

Table 1 above shows a peak frequency derived from sway of the center of gravity GL together with other peak frequencies, and indicates how many times the other peak frequencies are greater than the peak frequency derived from the sway of the center of gravity GL.

It is readily understood from Table 1 that clearly there are below-described two correlations (1) and (2) among a peak frequency derived from sway of the center of gravity GL, a peak frequency derived from sway of the center of gravity GM, and a peak frequency derived from sway of the center of gravity GT of each test subject. The correlation (1) is that the acceleration peak frequency ratios are the ratios of integral multiples. Specifically, the acceleration peak frequencies are linked such that the acceleration peak frequency derived from the sway of the center of gravity GM is about two times as great as the acceleration peak frequency derived from the sway of the center of gravity GL, and the acceleration peak frequency derived from the sway of the center of gravity GT is about three times as great as the acceleration peak frequency derived from the sway of the center of gravity GL. The correlation (2) is that the angular velocity peak frequency ratios are the ratios of odd multiples. Specifically, the angular velocity peak frequencies are linked such that the angular velocity peak frequency derived from the sway of the center of gravity GM is about three times as great as the angular velocity peak frequency derived from the sway of the center of gravity GL, and the angular velocity peak frequency derived from the sway of the center of gravity GT is about five times as great as the angular velocity peak frequency derived from the sway of the center of gravity GL.

The above facts mean that the sway of the center of gravity GL, the sway of the center of gravity GM, and the sway of the center of gravity GT are in stable resonation with each other. The reason for this is explained below.

According to Literature 2 ("*Mathematics for Physics*, 6-4 forced vibration" [Translated from Japanese.], authored by Miki Wadachi, published by Iwanami Shoten, Publishers, page 168), in a case where a source frequency that is the source of vibration is $f_0$, when restoring force acts on vibration of another frequency different from the source frequency $f_0$, if an integer n that holds an equation (3) shown below true exists, then the vibration of the other frequency is significant although the vibration of the source frequency $f_0$ is greater.

The above-described phenomenon is called stable resonation. That is, when sway has occurred due to stable resonation, it means that passive sway having a finite magnitude and corresponding to an integral multiple of the source frequency has occurred. It should be noted that the source of energy of the sway occurring due to stable resonation is the source sway. Accordingly, the magnitude of the sway occurring due to stable resonation is finite and does not diverge.

[Math. 3]

$$f = f n_0 \qquad (3)$$

It is understood from the correlation (1) and the correlation (2) that there is clearly a relationship represented by the equation (3) among a peak frequency derived from sway of the center of gravity GL, a peak frequency derived from sway of the center of gravity GM, and a peak frequency derived from sway of the center of gravity GT of each test subject.

As previously described, the center of gravity GL is positioned below the region of the spinal column spring base M, and the center of gravity GM is positioned below the region of the clavicle spring base T. Therefore, the spinal column spring base M and the clavicle spring base T do not affect the sway of the center of gravity corresponding to the other spring base positioned below the spinal column spring base M and the clavicle spring base T.

The lighter the mass, the quicker and smaller the sway of the center of gravity. Accordingly, when the sway of the center of gravity GL is in stable resonation with the sway of the center of gravity GM and the sway of the center of gravity GT at integral multiples of their peak frequencies, the center of gravity GM sways less and more quickly than the center of gravity GL, and the center of gravity GT sways less and more quickly than the center of gravity GM. From this, it is understood that while a person is moving, the body balance of the person is maintained autonomously.

Further, as shown in Table 1, the peak frequency of the angular velocity of the center of gravity GL is about ½ of the peak frequency of the acceleration of the center of gravity GL. Accordingly, under the conditions of the frequency ratios of integral multiples and odd multiples described in the correlation (1) and the correlation (2), unstable resonation of the sways of the respective three centers of gravity with each other is less likely to occur at least in a low frequency range of about several Hz to several tens of Hz. This is clearly indicated in FIGS. 2A and 2B, FIGS. 3A and 3B, and FIGS. 4A and 4B. It should be noted that, as previously described, "unstable resonation" means a phenomenon in which a combined amplitude of sway sources having different frequencies from each other becomes mathematically infinite or indefinite at a particular frequency. During unstable resonation, the amplitude of sway becomes infinite or indefinite. Accordingly, if unstable resonation occurs, there is a risk that the vibration system eventually becomes broken. Therefore, it is necessary to avoid unstable resonation as much as possible. Thus, unstable resonation is different from stable resonation, which is a phenomenon where passive sway having a finite magnitude occurs corresponding to a single source of sway.

In fact, in the data of each test subject, there is no overlap between the angular velocity peak frequencies appearing in the spectrum and the acceleration peak frequencies appearing in the spectrum. This is a proof that while a person is moving, the person utilizes stable resonation while avoiding unstable resonation.

As described above, it is considered that the center of gravity GL, the center of gravity GM, and the center of gravity GT existing in a person are in stable resonation with each other while maintaining independence from each other, and thereby the posture of the person is maintained properly. Specifically, even in a case where large motion of the lower extremity due to an activity performed by the person (e.g., walking, performing work, etc.) causes the center of gravity GL of the entire body, which is supported by the lower extremity spring base L, to sway, the sway of the center of gravity GM of the upper chest supported by the spinal column spring base M is more stable than the sway of the center of gravity GL owing to the above-described stable resonation phenomenon. Further, the sway of the center of gravity GT of the head supported by the clavicle spring base T is more stable than the sway of the center of gravity GM owing to the stable resonation phenomenon. In fact, when a person walks, the person hardly feels sway at their chest and head.

The present discloser conducted diligent studies, and as a result of the studies, by knowing the above-described stable resonation of sways of the centers of gravity existing in a person, the present discloser has found suitable determination criteria for determining the level of fatigue of the person. Consequently, the present discloser has arrived at a below-described aspect of the present disclosure.

Specifically, a determination device of a fourth aspect of the present disclosure is configured such that, in the determination device of the third aspect, in a case where the first amplitude is greater than the second amplitude, and the second amplitude is greater than the third amplitude, the controller may determine the level of fatigue of the person to be a normal level.

Specifically, in the above case, it is considered that the center of gravity GL, the center of gravity GM, and the center of gravity GT existing in the person are in stable resonation with each other while maintaining independence from each other, and thereby the posture of the person is maintained properly, i.e., the level of fatigue of the person is the normal level.

A determination device of a fifth aspect of the present disclosure is configured such that, in the determination device of the third aspect, in a case where the first amplitude is less than or equal to the second amplitude but greater than the third amplitude, and the first amplitude is greater than an average value of the second amplitude and the third amplitude, the controller may determine the level of fatigue of the person to be a warning level.

Specifically, in the above case, when the first amplitude corresponding to sway of the center of gravity GL of the entire body, the sway being caused by motion of the lower extremity due to an activity performed by the person (e.g., walking, performing work, etc.), is compared with the second amplitude corresponding to sway of the center of gravity GM existing at the upper chest of the person, the sway being caused due to the activity performed by the person, the second amplitude is greater than or equal to the first amplitude for the reason of, for example, tottering of the person. However, at this stage, since the first amplitude is greater than the average value of the second and third amplitudes, it is considered that the level of fatigue of the person is still the warning level where the center of gravity GL, the center of gravity GM, and the center of gravity GT existing in the person are in stable resonation with each other while maintaining independence from each other, and thereby the posture of the person is maintained. It should be noted that the average value of the second and third amplitudes corresponds to the maximum amplitude in a case where the sway direction of the center of gravity GM and the sway direction of the center of gravity GT coincide with each other.

A determination device of a sixth aspect of the present disclosure is configured such that, in the determination device of the third aspect, in a case where the first amplitude is less than or equal to the second amplitude but greater than the third amplitude, and the first amplitude is less than or equal to an average value of the second amplitude and the third amplitude, the controller may determine the level of fatigue of the person to be an abnormal level.

Specifically, in the above case, when the first amplitude corresponding to sway of the center of gravity GL of the entire body, the sway being caused by motion of the lower extremity due to an activity performed by the person (e.g., walking, performing work, etc.), is compared with the second amplitude corresponding to sway of the center of gravity GM existing at the upper chest of the person, the sway being caused due to the activity performed by the person, the second amplitude is greater than or equal to the first amplitude for the reason of, for example, tottering of the person. Also, the first amplitude is less than or equal to average value of the second and third amplitudes. When the person is in this state, it is considered that the level of fatigue of the person is the abnormal level where the center of gravity GM and the center of gravity GT existing in the person are not in stable resonation with each other during the motion of the lower extremity, and while the person is performing the activity, it is difficult to autonomously maintain the body balance.

[Background that has LED to a Posture Control Device of One Aspect of the Present Disclosure]

Figure 5:
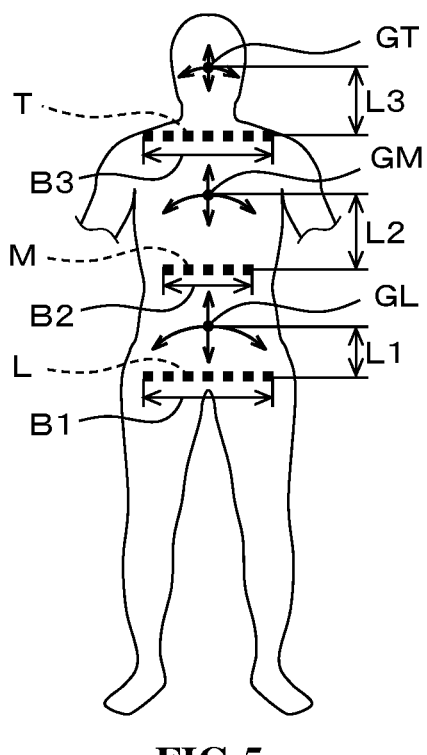
FIG. 5 shows one example of positions of centers of gravity existing in a person.

Similar to the center of gravity GL, the center of gravity GM, and the center of gravity GT shown in FIG. 5, the presence of three centers of gravity in a humanoid capable of bipedalism can be readily analogically inferred.

The present discloser conducted diligent studies, and as a result of the studies, the present discloser has found that posture control of a humanoid when the humanoid moves can be properly performed by utilizing the above-described stable resonation phenomenon of sways of the centers of gravity. Consequently, the present discloser has arrived at a below-described aspect of the present disclosure.

Specifically, a posture control device of a seventh aspect of the present disclosure is a posture control device for controlling a posture of a humanoid capable of bipedalism. The posture control device includes: a sway detector that detects sway of the humanoid when the humanoid moves; and a controller. The posture control device performs spectrum analysis by resolving sway data outputted from the sway detector into frequency components. In a spectrum obtained from the spectrum analysis, a first peak, a second peak, and a third peak sequentially appear in order of increasing frequency. Each of the first peak, the second peak, and the third peak is a peak that is derived from sway of a corresponding one of three centers of gravity existing in the humanoid. The controller controls the posture of the humanoid such that the sways of the respective three centers of gravity are in stable resonation with each other.

A posture control device of an eighth aspect of the present disclosure is configured such that, in the posture control device of the seventh aspect, the sway detector may include: an angular velocity sensor that detects an angular velocity of sway of the humanoid in a horizontal direction when the humanoid moves, the horizontal direction being orthogonal to a direction (that is hereinafter referred to as the perpendicular direction) in which gravitational force is exerted; and an accelerometer that detects acceleration of sway of the humanoid in the perpendicular direction when the humanoid moves. The first peak may include a first angular velocity peak and a first acceleration peak. The second peak may include a second angular velocity peak and a second acceleration peak. The third peak may include a third angular velocity peak and a third acceleration peak. Each of the first angular velocity peak, the second angular velocity peak, and the third angular velocity peak may be a peak that is derived from sway, in the horizontal direction, of a corresponding one of the three centers of gravity existing in the humanoid. Each of the first acceleration peak, the second acceleration peak, and the third acceleration peak may be a peak that is derived from sway, in the perpendicular direction, of a corresponding one of the three centers of gravity existing in the humanoid. The controller may control the posture of the humanoid such that the sways of the respective three centers of gravity in the horizontal direction are in stable resonation with each other at odd multiples, and such that the sways of the respective three centers of gravity in the perpendicular direction are in stable resonation with each other at integral multiples.

According to the above configurations, the posture control device of each of the above aspects is capable of properly controlling the posture of the humanoid by utilizing the stable resonation phenomenon of the sways of the respective three centers of gravity existing in the humanoid. That is, the posture of the humanoid can be maintained with a natural balance similar to that of a human.

Moreover, the posture control device of each of the above aspects makes it possible to reduce the number of sensors necessary for maintaining the posture of the humanoid and to simplify a control configuration for controlling the humanoid as compared to conventional art.

Hereinafter, specific examples of each aspect of the present disclosure are described with reference to the accompanying drawings. The specific examples described below are examples of the above-described aspects of the present disclosure. Therefore, shapes, components, the arrangement and the manner of connection of the components, etc., indicated below do not limit the above-described aspects of the present disclosure unless they are recited in the claims. Moreover, among the components described below, those that are not recited in any of the independent claims defining the most generic concept of the present disclosure are described as optional components. In the description below, in some cases, the description of components that are denoted by the same reference signs in the drawings may be omitted. The drawings show each component schematically in order to facilitate the understanding thereof. Therefore, in some cases, the drawings may not display precise shapes, precise dimensional ratios, etc. In the operations described below, for example, the order of steps can be changed as necessary. Furthermore, other known steps may be added as necessary.

Embodiment 1

[Device Configuration]

Figure 6:
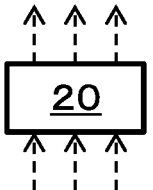
FIG. 6 shows one example of a determination device of Embodiment 1.
Figure 6:
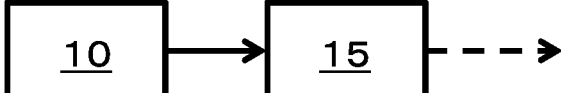

FIG. 6 shows one example of a determination device of Embodiment 1.

As shown in FIG. 6, a determination device 100 includes a sway detector 10, a transmitter 15, and a controller 20.

The sway detector 10 is a sensor that detects sway of a person when the person moves. It should be noted that the sway detector 10 has functions such as: a data conversion function of converting an analogue signal into a digital signal; a filtering function of removing unnecessary signals; and a function of amplifying signals. Since these functions are known, the description thereof is omitted herein. The sway detector 10 may be provided with a microprocessor that controls these functions.

In the determination device 100 of the present embodiment, the sway detector 10 includes an angular velocity sensor that detects, when a person moves, the angular velocity of sway of the person in the horizontal direction orthogonal to the direction in which the gravitational force is exerted (hereinafter, "perpendicular direction"). The angular velocity sensor may be configured in any manner, so long as the angular velocity sensor is capable of detecting the angular velocity of such sway as mentioned above that occurs when the person moves.

For example, the angular velocity sensor may be a gyro sensor of a vibratory type or an electrostatic capacitance type. The gyro sensor may be a uniaxial sensor, a biaxial sensor, or a triaxial sensor.

Figure 7:
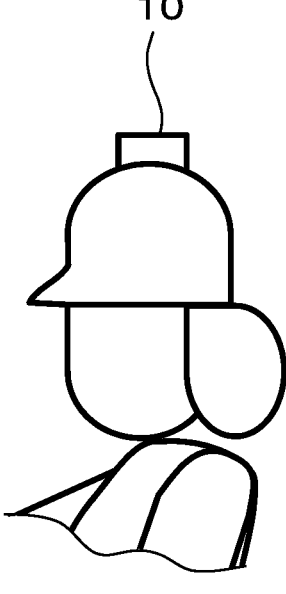
FIG. 7 shows one example of mounting of the sway detector of FIG. 6.

It should be noted that the sway detector 10 is configured to be mounted on a person, and the angular velocity sensor thereof is configured to detect, when the person moves, the angular velocity of sway of the person in the horizontal direction. The position to which the sway detector 10 is mounted is not particularly limited. For example, in a case where the sway detector 10 is mounted on a worker working at a civil engineering construction site, as shown in FIG. 7, the sway detector 10 can be readily fixed to the top of an engineer helmet worn by the worker.

The sway detector 10 further includes an accelerometer in addition to the above angular velocity sensor. The accelerometer may be configured in any manner, so long as the accelerometer is capable of detecting the acceleration of sway of a person in the perpendicular direction when the person moves.

The transmitter 15 wirelessly transmits sway data outputted from the sway detector 10 to a receiver of the controller 20. The transmitter 15 may be configured in any manner, so long as the transmitter 15 is capable of wirelessly transmitting the sway data to the receiver of the controller 20. For example, the transmitter 15 may be a Bluetooth (registered trademark) transmitter.

As previously described, the state of the body of a person is considered to be closely related to a physical phenomenon, specifically, closely related to whether the center of gravity of the body of the person is stable against external disturbance.

Accordingly, the determination device 100 of the present embodiment performs spectrum analysis (Fourier transformation) by resolving the sway data outputted from the sway detector 10 into frequency components. In a spectrum obtained from the spectrum analysis, a first peak, a second peak, and a third peak sequentially appear in order of increasing frequency. The controller 20 determines the state of the body of the person based on the first peak, the second peak, and the third peak.

Specifically, for example, when a person walks, the first peak, the second peak, and the third peak include the first angular velocity peak PD1, the second angular velocity peak PD2, and the third angular velocity peak PD3, respectively, as shown in FIG. 2A, FIG. 3A, and FIG. 4A. The first angular velocity peak PD1 is a peak that is derived from sway, in the horizontal direction, of the center of gravity GL (see FIG. 5) existing above the lower extremity of the person. The second angular velocity peak PD2 is a peak that is derived from sway, in the horizontal direction, of the center of gravity GM (see FIG. 5) existing at the upper chest of the person. The third angular velocity peak PD3 is a peak that is derived from sway, in the horizontal direction, of the center of gravity GT (see FIG. 5) existing at the head of the person.

At the time, the controller 20 determines the level of fatigue of the person based on a magnitude relationship among a first amplitude $A_1$ corresponding to the first angular velocity peak PD1, a second amplitude $A_m$ corresponding to the second angular velocity peak PD2, and a third amplitude $A_t$ corresponding to the third angular velocity peak PD3.

As one example, in a case where the first amplitude $A_1$ is greater than the second amplitude $A_m$, and the second amplitude $A_m$ is greater than the third amplitude $A_t$ (i.e., $A_1 > A_m > A_t$ as a first determination criterion), the controller 20 may determine the level of fatigue of the person to be a normal level.

Specifically, in the above case, as previously described, it is considered that the center of gravity GL, the center of gravity GM, and the center of gravity GT existing in the person are in stable resonation with each other while maintaining independence from each other, and thereby the posture of the person is maintained properly, i.e., the level of fatigue of the person is the normal level.

As another example, in a case where the first amplitude $A_1$ is less than or equal to the second amplitude $A_m$ but greater than the third amplitude $A_t$, and the first amplitude $A_1$ is greater than the average value of the second amplitude $A_m$ and the third amplitude $A_t$ (i.e., $A_m \geq A_1 > A_t$ and $A_1 > (A_m + A_t)/2$ as a second determination criterion), the controller 20 determines the level of fatigue of the person to be a warning level.

The average value of the second amplitude $A_m$ and the third amplitude $A_t$ corresponds to the maximum amplitude in a case where the sway direction of the center of gravity GM and the sway direction of the center of gravity GT coincide with each other.

Specifically, in the above case, when the first amplitude $A_1$ corresponding to sway of the center of gravity GL of the entire body, the sway being caused by motion of the lower extremity due to an activity performed by the person (e.g., walking, performing work, etc.), is compared with the second amplitude $A_m$ corresponding to sway of the center of gravity GM existing at the upper chest of the person, the sway being caused due to the activity performed by the person, the second amplitude $A_m$ is greater than or equal to the first amplitude $A_1$ for the reason of, for example, tottering of the person. However, at this stage, since the first amplitude $A_1$ is greater than the average value of the second and third amplitudes $A_m$ and $A_t$, it is considered that the level of fatigue of the person is still the warning level where the center of gravity GL, the center of gravity GM, and the center of gravity GT existing in the person are in stable resonation with each other while maintaining independence from each other, and thereby the posture of the person is maintained.

As yet another example, in a case where the first amplitude $A_1$ is less than or equal to the second amplitude $A_m$ but greater than the third amplitude $A_t$, and the first amplitude $A_1$ is less than or equal to the average value of the second amplitude $A_m$ and the third amplitude $A_t$ (i.e., $A_m \geq A_1 > A_t$ and $A_1 \leq (A_m + A_t)/2$ as a third determination criterion), the controller 20 determines the level of fatigue of the person to be an abnormal level.

Specifically, in the above case, when the first amplitude $A_1$ corresponding to sway of the center of gravity GL of the entire body, the sway being caused by motion of the lower extremity due to an activity performed by the person (e.g., walking, performing work, etc.), is compared with the second amplitude $A_m$ corresponding to sway of the center of gravity GM existing at the upper chest of the person, the sway being caused due to the activity performed by the person, the second amplitude $A_m$ is greater than or equal to the first amplitude $A_1$ for the reason of, for example, tottering of the person. Also, the first amplitude $A_1$ is less than or equal to the average value of the second and third amplitudes $A_m$ and $A_t$. When the person is in this state, it is considered that the level of fatigue of the person is the abnormal level where the center of gravity GM and the center of gravity GT existing in the person are not in stable resonation with each other during the motion of the lower extremity, and while the person is performing the activity, it is difficult to autonomously maintain the body balance.

It should be noted that the above-described first determination criterion, second determination criterion, and third determination criterion regarding the level of fatigue of a person are non-limiting examples. As yet another example, in a case where the first amplitude $A_1$ is less than or equal to the second amplitude $A_m$, and the second amplitude $A_m$ is less than or equal to the third amplitude $A_t$ (i.e., $A_1 \leq A_m \leq A_t$ as a fourth determination criterion), the controller 20 may determine the level of fatigue of the person to be an emergency level.

The controller 20 includes, for example, an arithmetic circuit (not shown) and a storage circuit (not shown) storing a program for performing the above-described determination. Examples of the arithmetic circuit include an MPU and CPU. Examples of the storage circuit include a memory. The controller 20 may be configured as a single controller performing centralized control, or may be configured as a plurality of controllers performing distributed control in cooperation with each other. It should be noted that the aforementioned program may realize not only the function of performing the determination by the controller 20 based on the determination criteria, but also the function of performing the spectrum analysis (Fourier transformation) by resolving the sway data outputted from the sway detector 10 into frequency components.

The controller 20 may include an operation setting device and a notification device that are not shown. The operation setting device is, for example, a keyboard. The notification device is, for example, a display-type notification device, or an audio notification device, for allowing a worker to recognize the result of the determination by the controller 20. The display notification device may be, but not limited to, a display panel screen or a lamp. The audio notification device may be, but not limited to, a speaker. The controller 20 thus configured may be, but not limited to, a portable information terminal (e.g., a personal computer) that can be carried around by a person.

[Operations]

Next, one example of operations performed by the determination device of Embodiment 1 is described with reference to the drawings.

Figure 8:
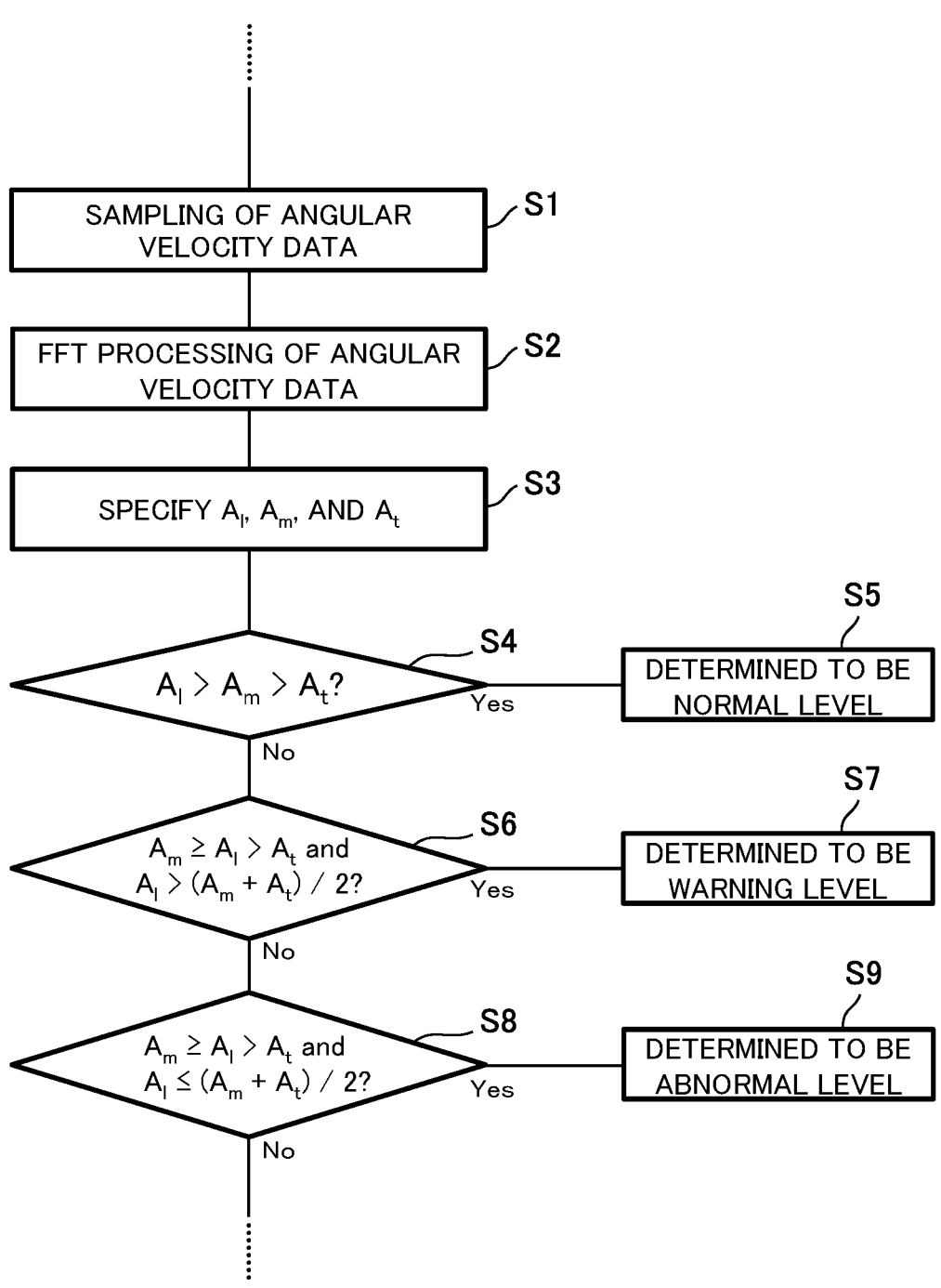
FIG. 8 is a flowchart showing one example of operations performed by the determination device of Embodiment 1.

FIG. 8 is a flowchart showing one example of operations performed by the determination device of Embodiment 1.

It should be noted that the operations described below may be performed, for example, as a result of the arithmetic circuit of the controller 20 reading out the program from the storage circuit of the controller 20. However, it is not essential that the operations described below be performed by the controller 20. Alternatively, part of the operations described below may be performed by a worker.

In a case where a worker performs work at, for example, a civil engineering construction site, the work is started when the worker wears an engineer helmet to which the sway detector 10 is fixed.

First, in step S1, sampling of angular velocity data outputted from the angular velocity sensor of the sway detector 10 is performed at an appropriate time.

Next, in step S2, the angular velocity data is resolved into frequency components, and thereby spectrum analysis (FFT processing of the angular velocity data) is performed. Consequently, as shown in FIG. 2A, FIG. 3A, and FIG. 4A, in a spectrum obtained from the spectrum analysis, the first angular velocity peak PD1, the second angular velocity peak PD2, and the third angular velocity peak PD3 sequentially appear in order of increasing frequency. Accordingly, the first amplitude $A_1$ corresponding to the first angular velocity peak PD1, the second amplitude $A_m$ corresponding to the second angular velocity peak PD2, and the third amplitude $A_t$ corresponding to the third angular velocity peak PD3 are specified (step S3).

Next, in step S4, it is determined whether or not the magnitude relationship among the first amplitude $A_1$, the second amplitude $A_m$, and the third amplitude $A_t$ obtained in step S3 satisfies the first determination criterion ($A_1 > A_m > A_t$).

If the above magnitude relationship satisfies the first determination criterion ("Yes" in step S4), then in step S5, the level of fatigue of the worker is determined to be the normal level. At the time, by using the notification device of the controller 20, the worker may be notified that the level of fatigue of the worker is the normal level. After the notification is performed, the flow may return to step S1, and the operations may be resumed from step S1 at an appropriate time.

If the above magnitude relationship does not satisfy the first determination criterion ("No" in step S4), the flow proceeds to the next step S6.

In step S6, it is determined whether or not the magnitude relationship among the first amplitude $A_1$, the second amplitude $A_m$, and the third amplitude $A_t$ obtained in step S3 satisfies the second determination criterion ($A_m \geq A_1 > A_t$ and $A_1 > (A_m + A_t)/2$).

If the above magnitude relationship satisfies the second determination criterion ("Yes" in step S6), then in step S7, the level of fatigue of the worker is determined to be the warning level. At the time, by using the notification device of the controller 20, the worker may be notified that the level of fatigue of the worker is the warning level. After the notification is performed, the flow may return to step S1, and the operations may be resumed from step S1 at an appropriate time.

If the above magnitude relationship does not satisfy the second determination criterion ("No" in step S6), the flow proceeds to the next step S8.

In step S8, it is determined whether or not the magnitude relationship among the first amplitude $A_1$, the second amplitude $A_m$, and the third amplitude $A_t$ obtained in step S3 satisfies the third determination criterion ($A_m \geq A_1 > A_t$ and $A_1 \leq (A_m + A_t)/2$).

If the above magnitude relationship satisfies the third determination criterion ("Yes" in step S8), then in step S7, the level of fatigue of the worker is determined to be the abnormal level. At the time, by using the notification device of the controller 20, the worker may be notified that the level of fatigue of the worker is the abnormal level.

After the notification is performed, or if the above magnitude relationship does not satisfy the third determination criterion ("No" in step S8), the flow may return to step S1, and the operations may be resumed from step S1 at an appropriate time.

[Experiments]

Described hereinafter is a case where the above-described first determination criterion, second determination criterion, and third determination criterion were applied to determine the level of fatigue of the test subject [3] during walking. Specifically, under a high-temperature and high-humidity condition in summer, the test subject [3] wearing an engineer helmet with the sway detector 10 fixed thereto walked, carrying a backpack with the controller 20 put therein, and thereby sway data outputted from the sway detector 10 was measured.

Figure 9A:
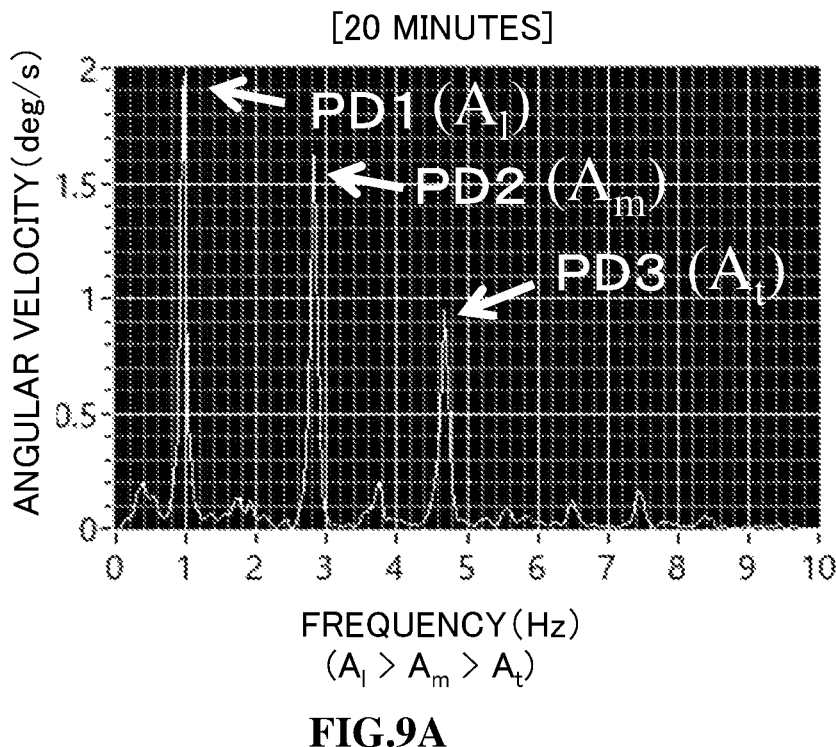
FIG. 9A shows one example of results of analyzing sway data outputted from the sway detector at an elapse of 20 minutes from the start of walking by the test subject [3].
Figure 9B:
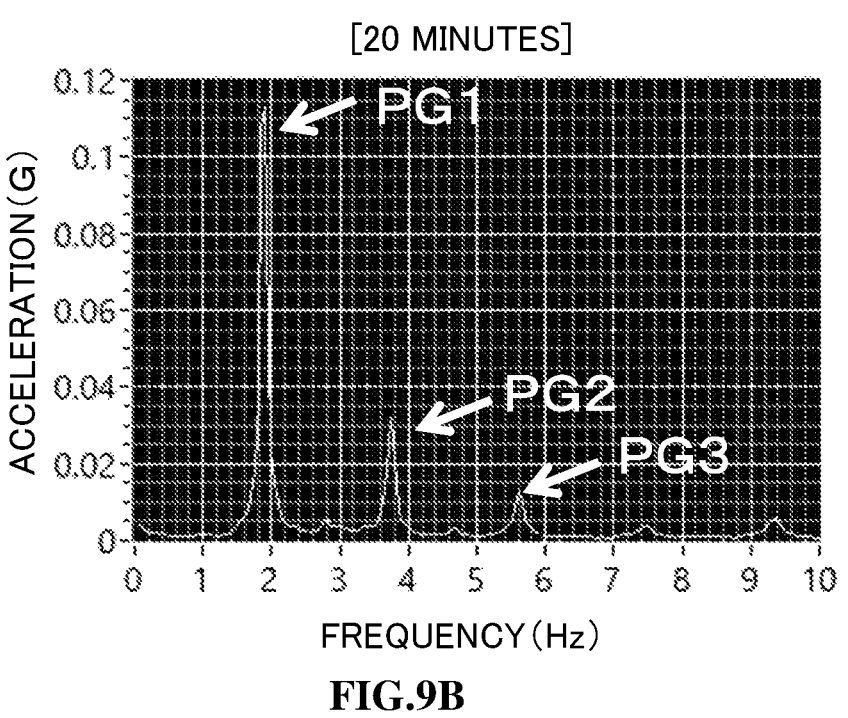
FIG. 9B shows one example of results of analyzing sway data outputted from the sway detector at an elapse of 20 minutes from the start of walking by the test subject [3].

FIG. 9A and FIG. 9B show one example of results of analyzing the sway data that was outputted from the sway detector at an elapse of 20 minutes from the start of the walking by the test subject [3].

Figure 10A:
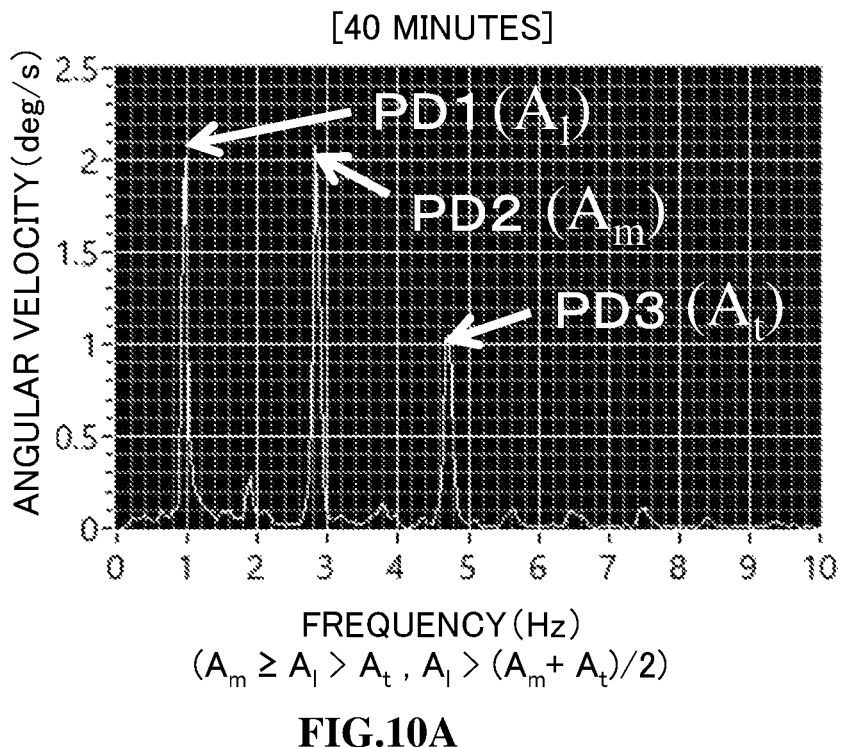
FIG. 10A shows one example of results of analyzing sway data outputted from the sway detector at an elapse of 40 minutes from the start of walking by the test subject [3].
Figure 10B:
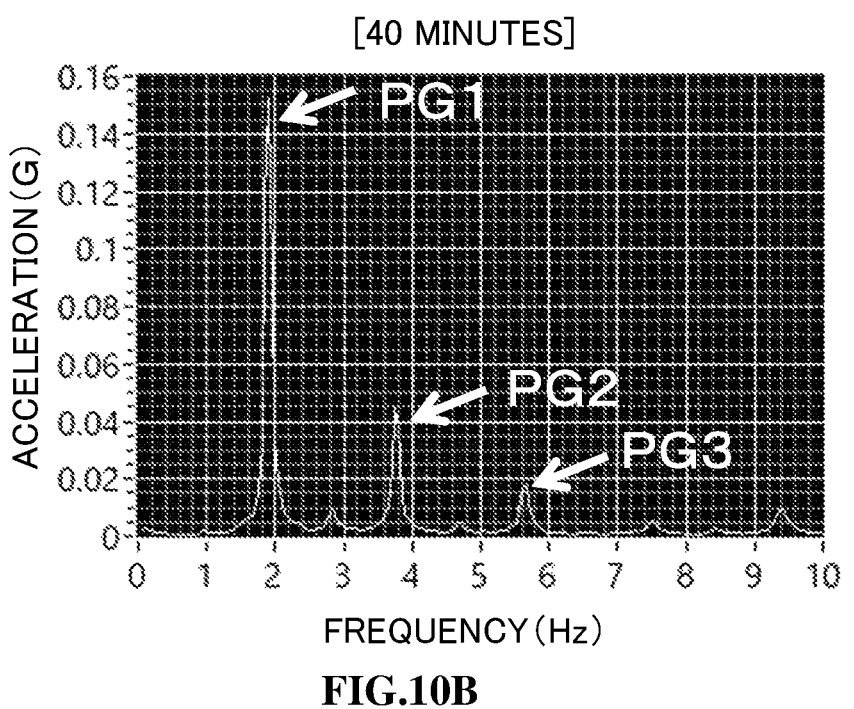
FIG. 10B shows one example of results of analyzing sway data outputted from the sway detector at an elapse of 40 minutes from the start of walking by the test subject [3].

FIG. 10A and FIG. 10B show one example of results of analyzing the sway data that was outputted from the sway detector at an elapse of 40 minutes from the start of the walking by the test subject [3].

Figure 11A:
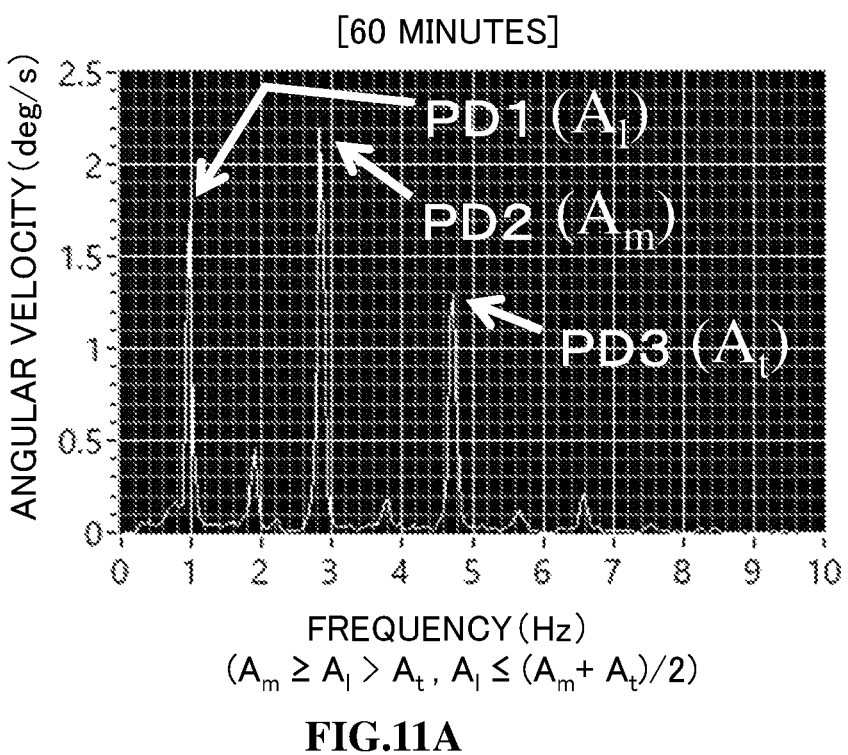
FIG. 11A shows one example of results of analyzing sway data outputted from the sway detector at an elapse of 60 minutes from the start of walking by the test subject [3].
Figure 11B:
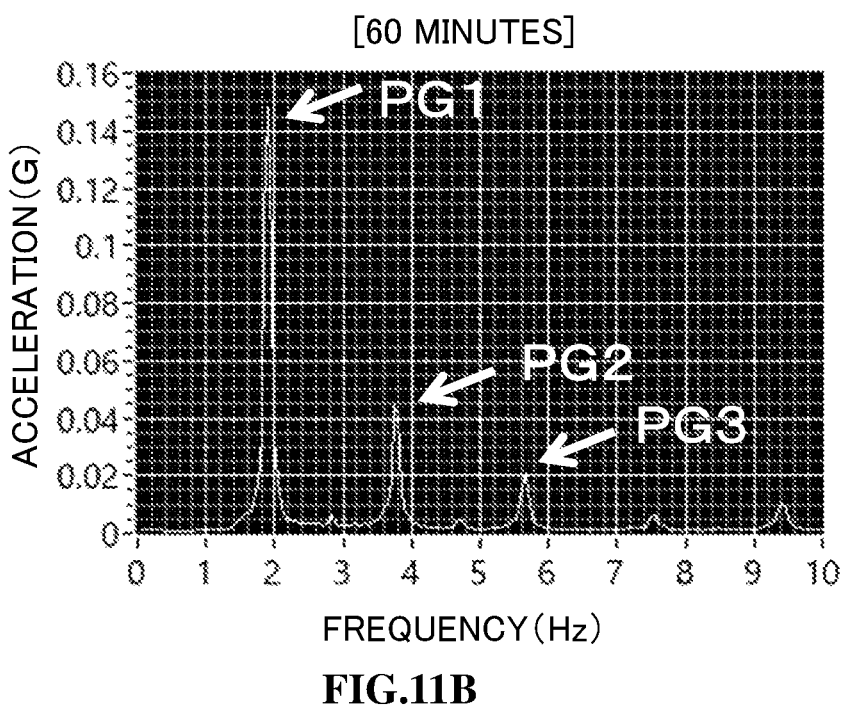
FIG. 11B shows one example of results of analyzing sway data outputted from the sway detector at an elapse of 60 minutes from the start of walking by the test subject [3].

FIG. 11A and FIG. 11B show one example of results of analyzing the sway data that was outputted from the sway detector at an elapse of 60 minutes from the start of the walking by the test subject [3].

Figure 12A:
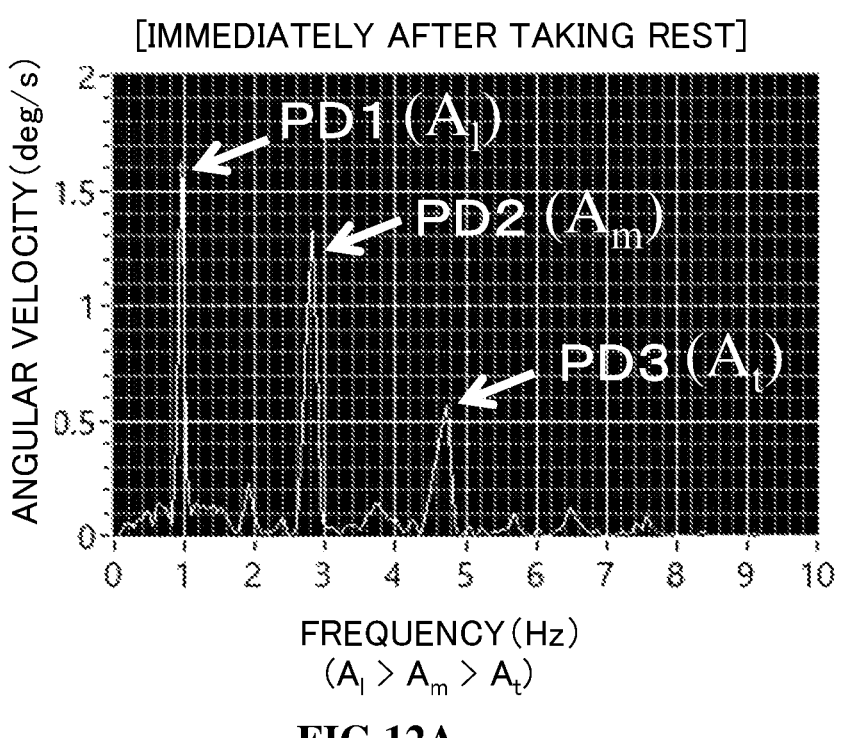
FIG. 12A shows one example of results of analyzing sway data outputted from the sway detector after an elapse of 60 minutes from the start of walking by the test subject [3] and immediately after the test subject [3] taking a rest and having water.
Figure 12B:
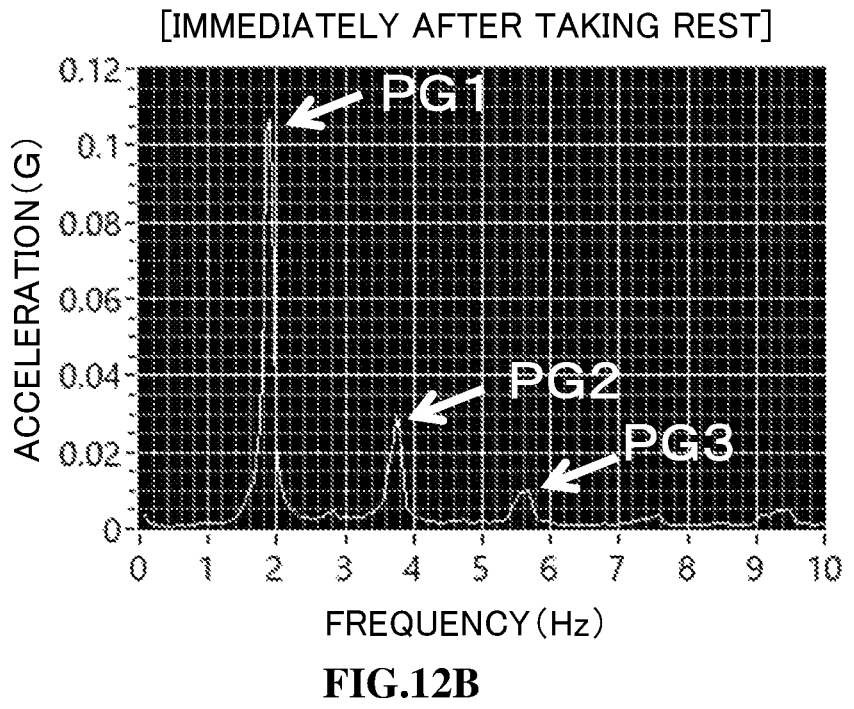
FIG. 12B shows one example of results of analyzing sway data outputted from the sway detector after an elapse of 60 minutes from the start of walking by the test subject [3] and immediately after the test subject [3] taking a rest and having water.

FIG. 12A and FIG. 12B show one example of results of analyzing the sway data that was outputted from the sway detector after an elapse of 60 minutes from the start of the walking by the test subject [3] and immediately after the test subject [3] taking a rest and having water.

Since the horizontal axis, the vertical axis, and the peak frequencies illustrated in each of FIG. 9A, FIG. 10A, FIG. 11A, and FIG. 12A are the same as those illustrated in FIG. 4A, the description thereof is omitted herein. Similarly, since the horizontal axis, the vertical axis, and the peak frequencies illustrated in each of FIG. 9B, FIG. 10B, FIG. 11B, and FIG. 12B are the same as those illustrated in FIG. 4B, the description thereof is omitted herein.

As shown in each of FIG. 9A, FIG. 10A, FIG. 11A, and FIG. 12A, in the spectrum obtained from the spectrum analysis, the first angular velocity peak PD1, the second angular velocity peak PD2, and the third angular velocity peak PD3 sequentially appear in order of increasing frequency. Accordingly, Table 2 below shows the first amplitude $A_1$ corresponding to the first angular velocity peak PD1, the second amplitude $A_m$ corresponding to the second angular velocity peak PD2, and the third amplitude $A_t$ corresponding to the third angular velocity peak PD3 at each of the elapsed times from the start of the walking by the test subject [3].

TABLE 2

| Walking time | $A_1$ | $A_m$ | $A_t$ | $(A_m + A_1)/2$ | Magnitude relationship among "$A_1$", "$A_m$", and "$A_t$" | Determination result |
|---|---|---|---|---|---|---|
| 20 min. | 2.131 | 1.652 | 0.958 | 1.305 | $A_1 > A_m > A_t$ | Normal level |
| 40 min. | 2.132 | 2.141 | 1.136 | 1.639 | $A_m \geq A_1 > A_t$ $A_1 > (A_m + A_t)/2$ | Warning level |
| 60 min. | 1.653 | 2.154 | 1.280 | 1.717 | $A_m \geq A_1 > A_t$ $A_1 \leq (A_m + A_t)/2$ | Abnormal level |
| Immediately after taking a rest | 1.742 | 1.353 | 0.568 | 0.961 | $A_1 > A_m > A_t$ | Normal level |

First, as shown in FIG. 9A and Table 2, at the elapse of 20 minutes from the start of the walking by the test subject [3], the first amplitude $A_1$, the second amplitude $A_m$, and the third amplitude $A_t$ were 2.131, 1.652, and 0.958, respectively. These numerical values satisfy the first determination criterion ($A_1 > A_m > A_t$).

These results indicate that, during the walking by the test subject [3], the center of gravity GL, the center of gravity GM, and the center of gravity GT existing in the test subject [3] were in stable resonation with each other while maintaining independence from each other, and thereby the posture of the test subject [3] was maintained properly.

Accordingly, at this stage, the level of fatigue of the test subject [3] from the walking was determined as the normal level.

It should be noted that, as shown in FIG. 9B, in the spectrum obtained from the spectrum analysis, the first acceleration peak PG1, the second acceleration peak PG2, and the third acceleration peak PG3 sequentially appear in order of increasing frequency.

Next, as shown in FIG. 10A and Table 2, at the elapse of 40 minutes from the start of the walking by the test subject [3], the first amplitude $A_1$, the second amplitude $A_m$, and the third amplitude $A_t$ were 2.132, 2.141, and 1.136, respectively. These numerical values satisfy the second determination criterion ($A_m \geq A_1 > A_t$ and $A_1 > (A_m + A_t)/2$).

These results indicate that, during the walking by the test subject [3], the second amplitude $A_m$ became greater than or equal to the first amplitude $A_1$ for the reason of, for example, tottering of the test subject [3]. However, in these results, the first amplitude $A_1$ was greater than the average value of the second amplitude $A_m$ and the third amplitude $A_t$. This means that the center of gravity GL, the center of gravity GM, and the center of gravity GT existing in the test subject [3] were in stable resonation with each other while maintaining independence from each other, and thereby the posture of the test subject [3] was maintained.

Accordingly, at this stage, the level of fatigue of the test subject [3] from the walking was determined as the warning level.

It should be noted that, as shown in FIG. 10B, in the spectrum obtained from the spectrum analysis, the first acceleration peak PG1, the second acceleration peak PG2, and the third acceleration peak PG3 sequentially appear in order of increasing frequency. These peaks in FIG. 10B do not exhibit changes from the peaks in FIG. 9B.

Next, as shown in FIG. 11A and Table 2, at the elapse of 60 minutes from the start of the walking by the test subject [3], the first amplitude $A_1$, the second amplitude $A_m$, and the third amplitude $A_t$ were 1.653, 2.154, and 1.280, respectively. These numerical values satisfy the third determination criterion ($A_m \geq A_1 > A_t$ and $A_1 \leq (A_m + A_t)/2$).

These results indicate that, during the walking by the test subject [3], the second amplitude $A_m$ became greater than or equal to the first amplitude $A_1$ for the reason of, for example, tottering of the test subject [3]. Also, in these results, the first amplitude $A_1$ was less than or equal to the average value of the second amplitude $A_m$ and the third amplitude $A_t$. This means that the center of gravity GM and the center of gravity GT existing in the test subject [3] were not in stable resonation with each other during the motion of the lower extremity, and during the walking by the test subject [3], it was difficult to autonomously maintain the body balance.

Accordingly, at this stage, the level of fatigue of the test subject [3] from the walking was determined as the abnormal level It should be noted that, as shown in FIG. 11B, in the spectrum obtained from the spectrum analysis, the first acceleration peak PG1, the second acceleration peak PG2, and the third acceleration peak PG3 sequentially appear in order of increasing frequency. These peaks in FIG. 11B do not exhibit changes from the peaks in FIG. 9B.

Next, as shown in FIG. 12A and Table 2, after the elapse of 60 minutes from the start of the walking by the test subject [3] and immediately after the test subject [3] taking a rest and having water, the first amplitude $A_1$, the second amplitude $A_m$, and the third amplitude $A_t$ were 1.742, 1.353, and 0.568, respectively. These numerical values satisfy the first determination criterion ($A_1 > A_m > A_t$).

These results indicate that, during the walking by the test subject [3], the center of gravity GL, the center of gravity GM, and the center of gravity GT existing in the test subject [3] were in stable resonation with each other while maintaining independence from each other, and thereby the posture of the test subject [3] was maintained properly.

Accordingly, at this stage, the level of fatigue of the test subject [3] from the walking was determined to have become the normal level again as a result of the test subject [3] recovering from the fatigue by taking a sufficient rest.

It should be noted that, as shown in FIG. 12B, in the spectrum obtained from the spectrum analysis, the first acceleration peak PG1, the second acceleration peak PG2, and the third acceleration peak PG3 sequentially appear in order of increasing frequency. These peaks in FIG. 12B do not exhibit changes from the peaks in FIG. 9B.

As described above, the determination device 100 of the present embodiment is capable of determining the state of the body of a person more precisely and in a simpler manner than conventional art.

For example, at civil engineering construction sites, due to workers' accumulated fatigue caused by a high-temperature and high-humidity condition in summer, various problems occur, such as deterioration in workers' physical condition, lowered work efficiency, and the occurrence of errors during the work. In recent years, these problems have been drawing attention. Generally known methods for determining the level of fatigue of a person include blood sugar level detection, heart rate measurement, etc. However, these data are significantly affected by, for example, lifestyle habits of individuals. Therefore, with these data, it is difficult to clearly indicate the level of fatigue of a person based on, for example, standardized numerical value ranges or standardized indexes. Moreover, it is impossible to measure the accumulation of fatigue of a person in real time with existing medical determination in which the determination is made by performing a close examination of the person at a hospital. Thus, such way of medical determination is not suitable for determining the level of fatigue of a person who works at, for example, a work site in the civil engineering construction industry or logistics industry.

On the other hand, the determination device 100 of the present embodiment is capable of properly determining the level of fatigue of a person based on universal criteria that are related to sways of the centers of gravity existing in the person and that are hardly affected by, for example, the lifestyle habits of individuals. Further, according to the determination device 100 of the present embodiment, for example, at a work site in the civil engineering construction industry or logistics industry, by merely attaching the sway detector 10 to a worker, the level of fatigue of the worker can be readily determined in real time.

(Variation)

In the present embodiment, the description has been given of a case where the controller 20 uses the sway detector 10 to detect sways of the centers of gravity existing in a person, the sways being caused due to an activity performed by the person (e.g., walking, performing work, etc.), thereby determining the level of fatigue of the person.

Alternatively, the controller 20 may use the sway detector 10 to detect sways of the centers of gravity existing in a person, the sways being caused due to an activity performed by the person (e.g., walking, performing work, etc.), thereby determining, for example, the state of health of the person.

Specifically, for example, it is often the case that in an unhealthy obese person, the position of the center of gravity GL of the entire body supported by the lower extremity spring base L, and the position of the center of gravity GM of the upper chest supported by the spinal column spring base M, are closer to each other than in a healthy person. It is also often the case that in an unhealthy obese person, the position of the lower extremity spring base L and the position of the center of gravity GL are closer to each other than in a healthy person. Accordingly, in the case of an unhealthy obese person, the first peak, the second peak, and the third peak sequentially appearing in order of increasing frequency in the spectrum obtained from the spectrum analysis (Fourier transformation) that is performed by resolving the sway data outputted from the sway detector 10 into frequency components are considered to be different from those in the case of a healthy person.

Therefore, the controller 20 can determine the state of health of a person based on the first peak, the second peak, and the third peak.

Other than the above features, the determination device 100 of the present variation may be the same as the determination device 100 of Embodiment 1.

Embodiment 2

Figure 13:
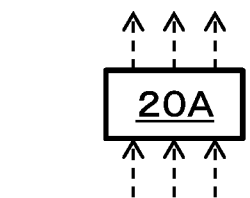
FIG. 13 shows one example of a posture control device of Embodiment 2.
Figure 13:
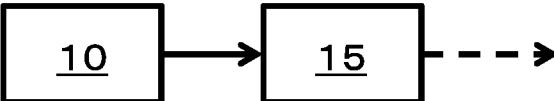

FIG. 13 shows one example of a posture control device of Embodiment 2.

As shown in FIG. 13, a posture control device 200 includes the sway detector 10, the transmitter 15, and a controller 20A.

Since the sway detector 10 and the transmitter 15 are the same as those of Embodiment 1, the description thereof is omitted herein.

As previously explained, similar to the center of gravity GL, the center of gravity GM, and the center of gravity GT shown in FIG. 5, the presence of three centers of gravity in a humanoid capable of bipedalism can be readily analogically inferred.

Accordingly, when a humanoid to which the sway detector 10 is attached moves, the posture control device 200 of the present embodiment performs spectrum analysis (Fourier transformation) by resolving sway data outputted from the sway detector 10 into frequency components. In a spectrum obtained from the spectrum analysis, a first peak, a second peak, and a third peak sequentially appear in order of increasing frequency. Each of the first peak, the second peak, and the third peak is a peak that is derived from sway of a corresponding one of the three centers of gravity existing in the humanoid (not shown). The controller 20A controls the posture of the humanoid such that the sways of the respective three centers of gravity existing in the humanoid are in stable resonation with each other.

To be specific, the first peak includes the first angular velocity peak PD1 and the first acceleration peak PG1; the second peak includes the second angular velocity peak PD2 and the second acceleration peak PG2; and the third peak includes the third angular velocity peak PD3 and the third acceleration peak PG3. Each of the first angular velocity peak PD1, the second angular velocity peak PD2, and the third angular velocity peak PD3 is a peak that is derived from sway, in the horizontal direction, of a corresponding one of the three centers of gravity existing in the humanoid. Each of the first acceleration peak PG1, the second acceleration peak PG2, and the third acceleration peak PG3 is a peak that is derived from sway, in the perpendicular direction, of a corresponding one of the three centers of gravity existing in the humanoid.

At the time, the controller 20A controls the posture of the humanoid such that the sways, in the horizontal direction, of the respective three centers of gravity existing in the humanoid are in stable resonation with each other at odd multiples, and such that the sways, in the perpendicular direction, of the respective three centers of gravity are in stable resonation with each other at integral multiples. It should be noted that, in this case, the controller 20A controls the posture of the humanoid such that the sways, in the horizontal direction, of the respective three centers of gravity existing in the humanoid, and the sways, in the perpendicular direction, of the respective three centers of gravity existing in the humanoid, are hindered from being in unstable resonation with each other. This is realized, for example, in the following manner; a frequency corresponding to the lowest-frequency sway among the sways of the three centers of gravity in the horizontal direction, and a frequency corresponding to the lowest-frequency sway among the sways of the three centers of gravity in the perpendicular direction, are shifted from each other by a predetermined frequency. As one example, the former frequency may be about ½ of the latter frequency.

The controller 20A includes, for example, an arithmetic circuit (not shown) and a storage circuit (not shown) storing a program for performing the above-described posture control. Examples of the arithmetic circuit include an MPU and CPU. Examples of the storage circuit include a memory. The controller 20A may be configured as a single controller performing centralized control, or may be configured as a plurality of controllers performing distributed control in cooperation with each other.

As described above, the posture control device 200 of the present embodiment is capable of properly controlling the posture of a humanoid by utilizing the stable resonation phenomenon of the sways of the respective three centers of gravity existing in the humanoid. That is, the posture of the humanoid can be maintained with a natural balance similar to that of a human.

Moreover, the posture control device 200 of the present embodiment makes it possible to reduce the number of sensors necessary for maintaining the posture of a humanoid and to simplify a control configuration for controlling the humanoid as compared to conventional art.

It should be noted that Embodiment 1, the variation of Embodiment 1, and Embodiment 2 may be combined with each other, so long as the combined features do not contradict with each other.

From the foregoing description, numerous modifications and other embodiments of the present disclosure are obvious to those skilled in the art. Accordingly, the foregoing description is to be construed as illustrative only, and is provided for the purpose of teaching those skilled in the art the best mode for carrying out the present disclosure. The structural and/or functional details may be substantially modified without departing from the scope of the present disclosure.

INDUSTRIAL APPLICABILITY

One aspect of the present disclosure is applicable to a determination device that is capable of determining the state of the body of a person more precisely and in a simpler manner than conventional art.

REFERENCE CHARACTERS LIST

10: sway detector
15: transmitter
20: controller
20A: controller
100: determination device
200: posture control device
GL: center of gravity
GM: center of gravity
GT: center of gravity
L: lower extremity spring base
M: spinal column spring base
T: clavicle spring base

The invention claimed is:
1. A determination device comprising:
a sway detector that detects sway of a person in a horizontal direction when the person moves, the horizontal direction being orthogonal to a direction in which gravitational force is exerted and to a walking direction of the person; and
a controller, wherein
the determination device performs spectrum analysis by resolving sway data outputted from the sway detector into frequency components based on Fourier transformation,
in a spectrum obtained from the spectrum analysis, a first peak, a second peak, and a third peak sequentially appear in order of increasing frequency, each of the first peak, the second peak, and the third peak being a peak that is derived from sway of a corresponding one of centers of gravity existing in the person,
the sway detector includes an angular velocity sensor that detects an angular velocity of sway of the person in the horizontal direction when the person moves,
the first peak, the second peak, and the third peak include a first angular velocity peak, a second angular velocity peak, and a third angular velocity peak, respectively,
the first angular velocity peak is a peak that is derived from sway, in the horizontal direction, of a center of gravity existing above a lower extremity of the person,
the second angular velocity peak is a peak that is derived from sway, in the horizontal direction, of a center of gravity existing at an upper chest of the person,
the third angular velocity peak is a peak that is derived from sway, in the horizontal direction, of a center of gravity existing at a head of the person, and
the controller determines a state to maintain a posture of the person based on the first peak, the second peak, and the third peak.
2. The determination device according to claim 1, wherein the controller determines a level of fatigue of the person based on a magnitude relationship among a first amplitude corresponding to the first angular velocity peak, a second amplitude corresponding to the second angular velocity peak, and a third amplitude corresponding to the third angular velocity peak.
3. The determination device according to claim 2, wherein in a case where the first amplitude is greater than the second amplitude, and the second amplitude is greater than the third amplitude, the controller determines the level of fatigue of the person to be a normal level.
4. The determination device according to claim 2, wherein in a case where the first amplitude is less than or equal to the second amplitude but greater than the third amplitude, and the first amplitude is greater than an average value of the second amplitude and the third amplitude, the controller determines the level of fatigue of the person to be a warning level.
5. The determination device according to claim 2, wherein in a case where the first amplitude is less than or equal to the second amplitude but greater than the third amplitude, and the first amplitude is less than or equal to an average value of the second amplitude and the third amplitude, the controller determines the level of fatigue of the person to be an abnormal level.
6. A posture control device for controlling a posture of a humanoid capable of bipedalism, the posture control device comprising:
a sway detector that detects sway of the humanoid in a horizontal direction when the humanoid moves, the horizontal direction being orthogonal to a direction (hereinafter referred to as the perpendicular direction) in which gravitational force is exerted and to a walking direction of the humanoid; and
a controller, wherein
the posture control device performs spectrum analysis by resolving sway data outputted from the sway detector into frequency components based on Fourier transformation,
in a spectrum obtained from the spectrum analysis, a first peak, a second peak, and a third peak sequentially appear in order of increasing frequency,
each of the first peak, the second peak, and the third peak is a peak that is derived from sway of a corresponding one of three centers of gravity existing in the humanoid, the sway detector includes:

an angular velocity sensor that detects an angular velocity of sway of the humanoid in the horizontal direction when the humanoid moves; and an accelerometer that detects acceleration of sway of the humanoid in the perpendicular direction when the humanoid moves, the first peak includes a first angular velocity peak and a first acceleration peak, the second peak includes a second angular velocity peak and a second acceleration peak, the third peak includes a third angular velocity peak and a third acceleration peak, each of the first angular velocity peak, the second angular velocity peak, and the third angular velocity peak is a peak that is derived from sway, in the horizontal direction, of a corresponding one of the three centers of gravity existing in the humanoid, each of the first acceleration peak, the second acceleration peak, and the third acceleration peak is a peak that is derived from sway, in the perpendicular direction, of a corresponding one of the three centers of gravity existing in the humanoid, and the controller controls the posture of the humanoid such that the sways of the respective three centers of gravity in the horizontal direction are in stable resonation with each other at odd multiples, and such that the sways of the respective three centers of gravity in the perpendicular direction are in stable resonation with each other at integral multiples.

\* \* \* \* \*